United States Patent [19]

Shieh

[11] Patent Number: 5,377,363
[45] Date of Patent: Jan. 3, 1995

[54] AUTOMATIC LAVATORY DETERGENT AND PERFUME DISPENSER

[76] Inventor: Snoopy Shieh, 6-2 Fl., No. 11, Ming Chuan W. Rd., Taipei, Taiwan, Prov. of China

[21] Appl. No.: 207,695

[22] Filed: Mar. 9, 1994

[51] Int. Cl.6 .......................... E03D 9/03; E03D 5/10
[52] U.S. Cl. ........................................ 4/313; 4/304; 4/222; 4/226.1; 422/124
[58] Field of Search ................ 4/222, 223, 224, 226.1, 4/228.1, 302, 304, 305, 313, 309; 222/67; 422/124, 305

[56] References Cited

U.S. PATENT DOCUMENTS

| | | | |
|---|---|---|---|
| 2,472,383 | 6/1949 | Owens | 4/222 |
| 2,682,059 | 6/1954 | Grossmann | 4/226.1 |
| 4,383,951 | 5/1983 | Palson | 422/124 |
| 4,429,809 | 2/1984 | Bousgarbies | 222/67 |
| 5,125,119 | 6/1992 | Munoz | 4/228.1 X |
| 5,251,340 | 10/1993 | Su-Land | 4/304 |
| 5,269,028 | 12/1993 | Liao | 4/313 |

FOREIGN PATENT DOCUMENTS 0338825 10/1989 European Pat. Off. ............ 4/226.1

Primary Examiner—Robert M. Fetsuga
Attorney, Agent, or Firm—Bacon & Thomas

[57] ABSTRACT

An automatic lavatory detergent and perfume dispenser including a control circuit assembly, a detergent dispensing device controlled to send a fixed amount of a detergent into a water container being linked to the flush pipe of a lavatory flushing system, and a DC motor fan operated perfume dispensing device controlled to spray a liquid perfume into the air, and a control circuit assembly to detect the approach of human bodies through an infrared monitor and to actuate the detergent dispensing device and the perfume dispensing device upon the detection of the approach of a human body.

2 Claims, 10 Drawing Sheets

AUTOMATIC LAVATORY DETERGENT AND PERFUME DISPENSER

BACKGROUND OF THE INVENTION

The present invention relates to an automatic lavatory detergent and perfume dispenser which sends a fixed amount of a detergent into the lavatory and sprays a liquid perfume into the air each time the flushing system is operated.

The techniques of mounting a chemical dispensing device on the lavatory to send a detergent into the lavatory upon each use of the lavatory, have been known and described in U.S. Pat. Nos. 1,447,289; 1,643,286; 3,417,410; 3,913,151.

According to "Disinfector attachment for the flushing arrangements of water closets" of U.S. Pat. No. 1,447,289, a water container is provided to take water from the flush pipe of the flushing arrangement of a water closet, having a float on the inside. The floats opens a valve to let a soluble perfume enter the water container, when water in the water container reaches full water level. Because this disinfectant is immediately carried away and disappeared in the sewerage system, little amount of the disinfectant is maintained working.

According to "Automatic flush tank and deodorizer" of U.S. Pat. No. 1,643,286, when the outlet valve of the flush tank is opened, the outlet valve of the deodorizer tank will also be opened so as to discharge a certain amount of deodorant into the water passing from the flush tank. This structure of deodorizer dispensing device is bulk and it produces noises during its operation. Another drawback of this structure of deodorizer dispensing device is that is does not fit all types of lavatories.

According to "Chemical dispenser" of U.S. Pat. No. 3,417,410, there is provided a dispenser of a chemical into a flush valve operated water pipe leading to a urinal or toilet, in which an adjustable water inlet tube leads from the water pipe to a container containing the chemical, and a separate outlet tube carries the water mixed with the chemical in the container to the water pipe, to exit to the urinal or toilet, substantially simultaneously, and with the outlet tube so constructed that a after-flow and streaking are eliminated.

According to "apparatus for dispensing metered quantity of liquid" of U.S. Pat. No. 3,913,151, the apparatus comprises a liquid-containing reservoir which fits inside the toilet tank. The reservoir includes a metering chamber with input and exit ports respectively actuated by a pair of nested floats which extend downwardly into the toilet tank and which are actuated, seriatim, by the rising level of water in the tank after each flush.

The aforesaid chemical dispensing devices simply send the deodorizer or the like into the flush pipe but do not provide any function to send deodorizer or the like into the air. Therefore, these devices cannot purify the air. Furthermore, these devices work only when the flushing arrangement is operated, i.e., they do not automatically and intermittently dispense the chemical.

SUMMARY OF THE INVENTION

The present invention has been accomplished to provide an automatic lavatory detergent and perfume dispenser which eliminates the aforesaid drawbacks. According to one aspect of the present invention, the automatic lavatory detergent and perfume dispenser comprises a detergent dispensing device controlled by water pressure to send a fixed amount of a detergent into a water container being linked to the flush pipe of a lavatory flushing system, and a DC motor fan operated perfume dispensing device controlled to spray a liquid perfume into the air. According to another aspect of the present invention, the housing of the automatic lavatory detergent and perfume dispenser has a view window for allowing the user to check the existing amount of the detergent in the detergent container and the perfume in the perfume container. According to still another aspect of the present invention, the automatic lavatory detergent and perfume dispenser further comprises a control circuit assembly to detect the approach of human bodies through an infrared monitor and to actuate the detergent dispensing device and the perfume dispensing device upon the detection of the approach of a human body.

DETAILED DESCRIPTION OF THE PREFERRED EMBODIMENT

Figure 1:
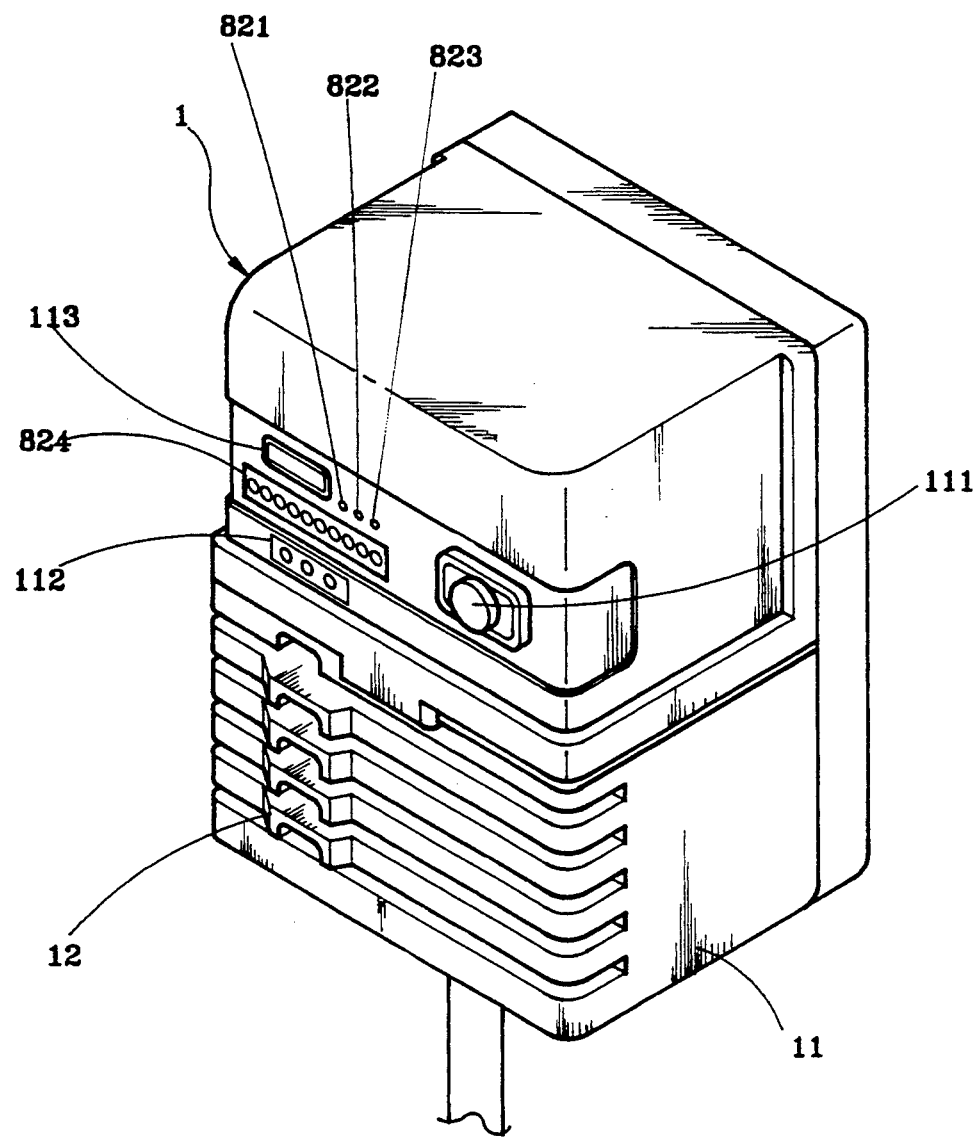
FIG. 1 is an elevational view of an automatic lavatory detergent and perfume dispenser according to the preferred embodiment of the present invention.

Referring to FIG. 1, the automatic lavatory detergent and perfume dispenser comprises a housing 1 having a view window 111 on the front panel thereof at one corner, through which the internal arrangement of the dispenser is viewed, an indicator lamp mirror 113, and a shutter 12 on the front panel at another corner, through which a perfume is sent out.

Figure 2:
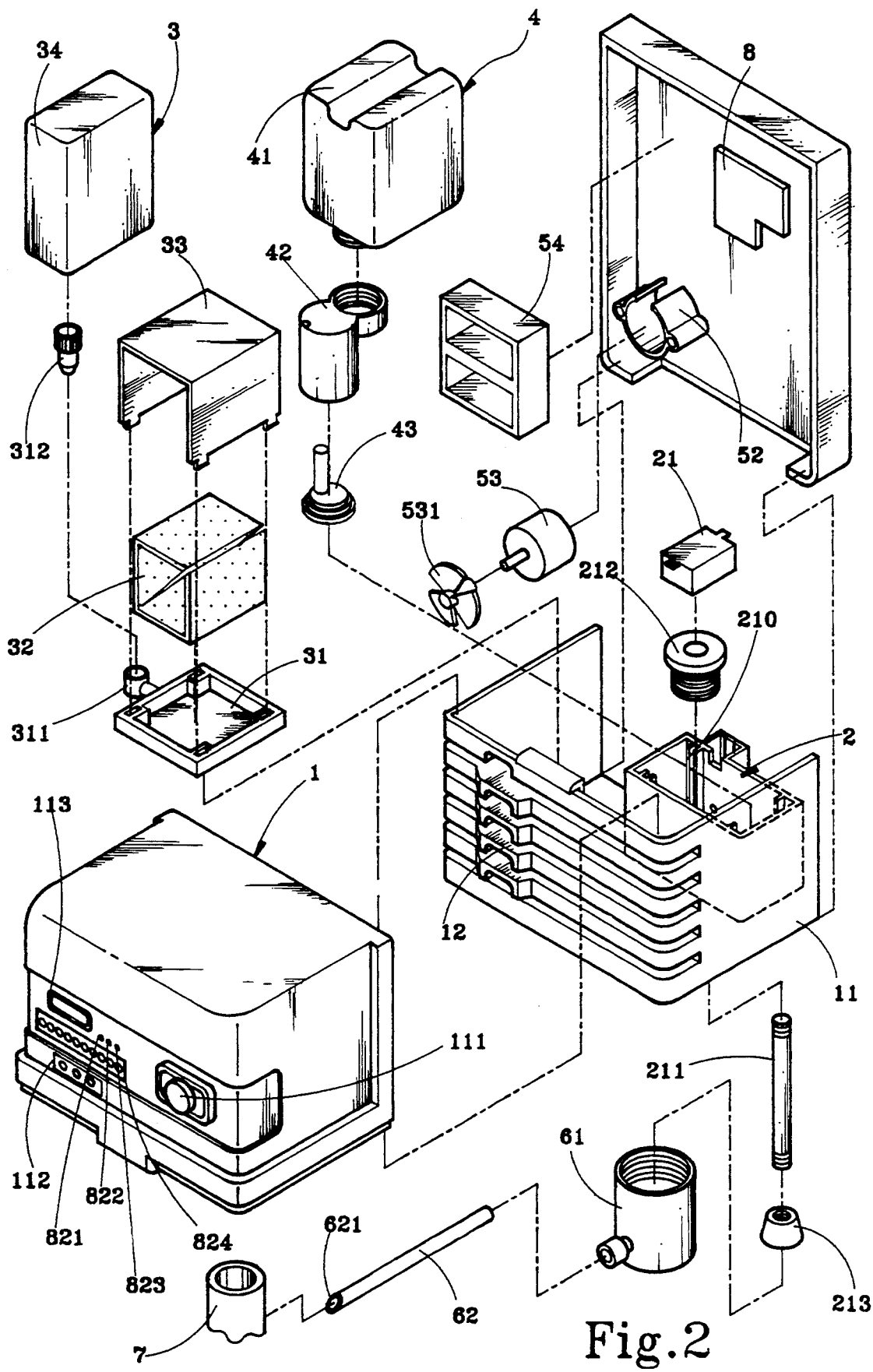
FIG. 2 is an exploded view of the automatic lavatory detergent and perfume dispenser shown in FIG. 1.
Figure 3:
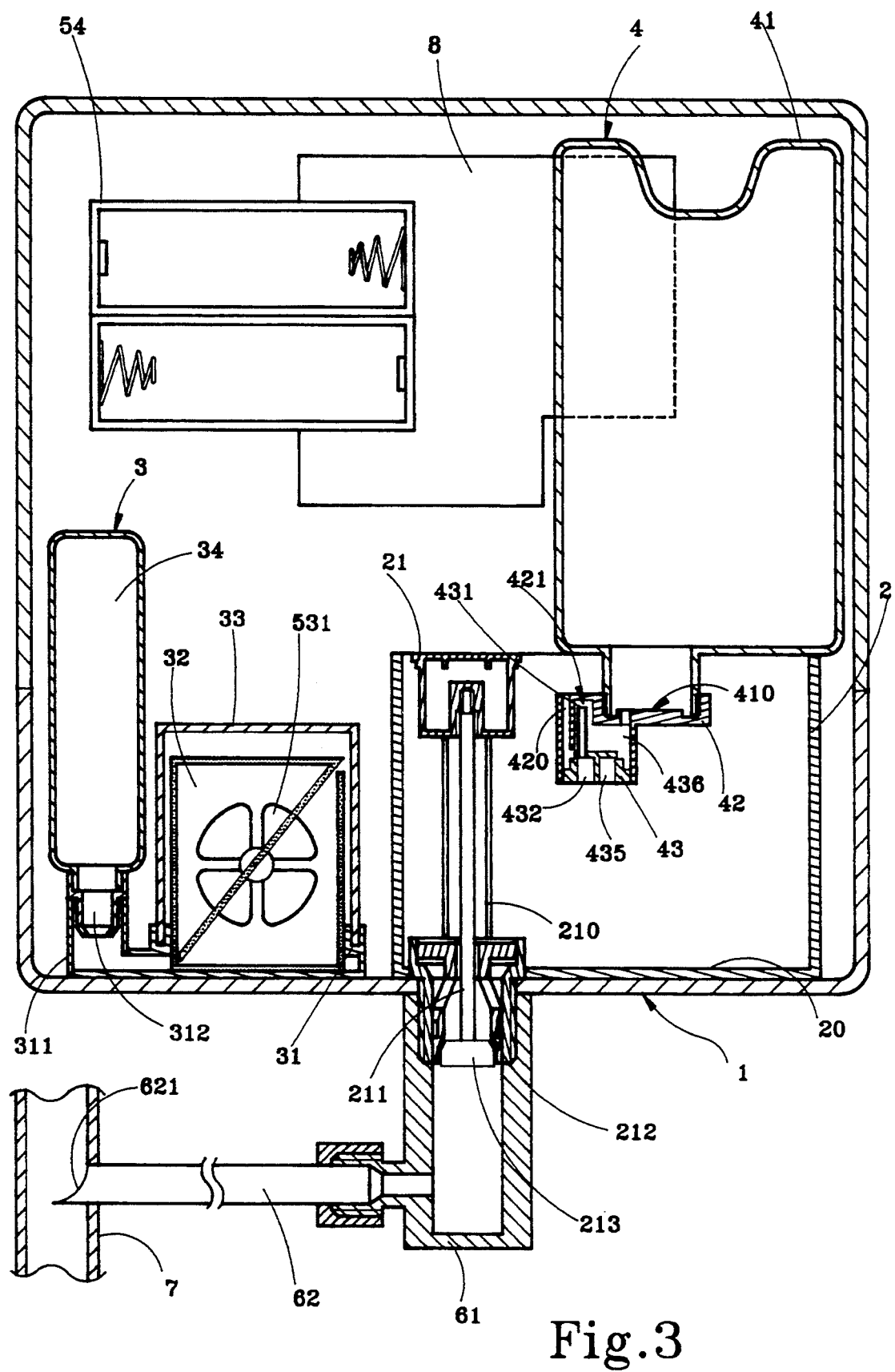
FIG. 3 is a sectional view showing the internal arrangement of the automatic lavatory detergent and perfume dispenser shown in FIG. 1.

Referring to FIGS. 2 and 3, a top-open water container 2 is mounted on the horizontal wall of a base frame 11 inside the housing 1. The water container 2 comprises a valve seat 212 on the bottom 20 thereof for passing water. A water guide device is provided to guide flushing water into the water container 2. The water guide comprises a guide pipe 62 connected to the valve seat 212 by a pipe connector 61. The water guide pipe 62 has a beveled front end 621 inserted into a hole (not shown) on the flush pipe 7 of a flushing system for guiding water from the flushing system into the water container 2. A float 21 is disposed in a vertical track 210 inside the water container 2 and mounted on an upright rod 211 at the top. The bottom end of the upright rod 211 is coupled with a valve cone 213. The valve cone 213 is received inside the pipe connector 61 and moved to control the passage of the valve seat 212. A detergent dispensing device 4 is fastened inside the housing 1 and disposed above the water container 1. When water is guided into the water container 2, the detergent dispensing device 4 will send out a fixed amount of the detergent being contained therein to mix with water in the water container 2, and then the detergent solution will be drawn away from the water container 2 into the flush pipe 7 again. The detergent dispensing device 4 comprises a transparent detergent container 41, which holds a detergent (such as quaternary ammonium compound) and has a bottom opening 410 (see FIG. 7), a dispensing cap 42 fastened to the bottom opening 410 of the transparent detergent container 41 and disposed inside the water container 2 at the top, and a dispensing valve 43 fastened to the dispensing cap 42 and moved by water to control the passage through the bottom opening 410. The dispensing operation of the detergent dispensing device 4 will be explained further.

Figure 6:
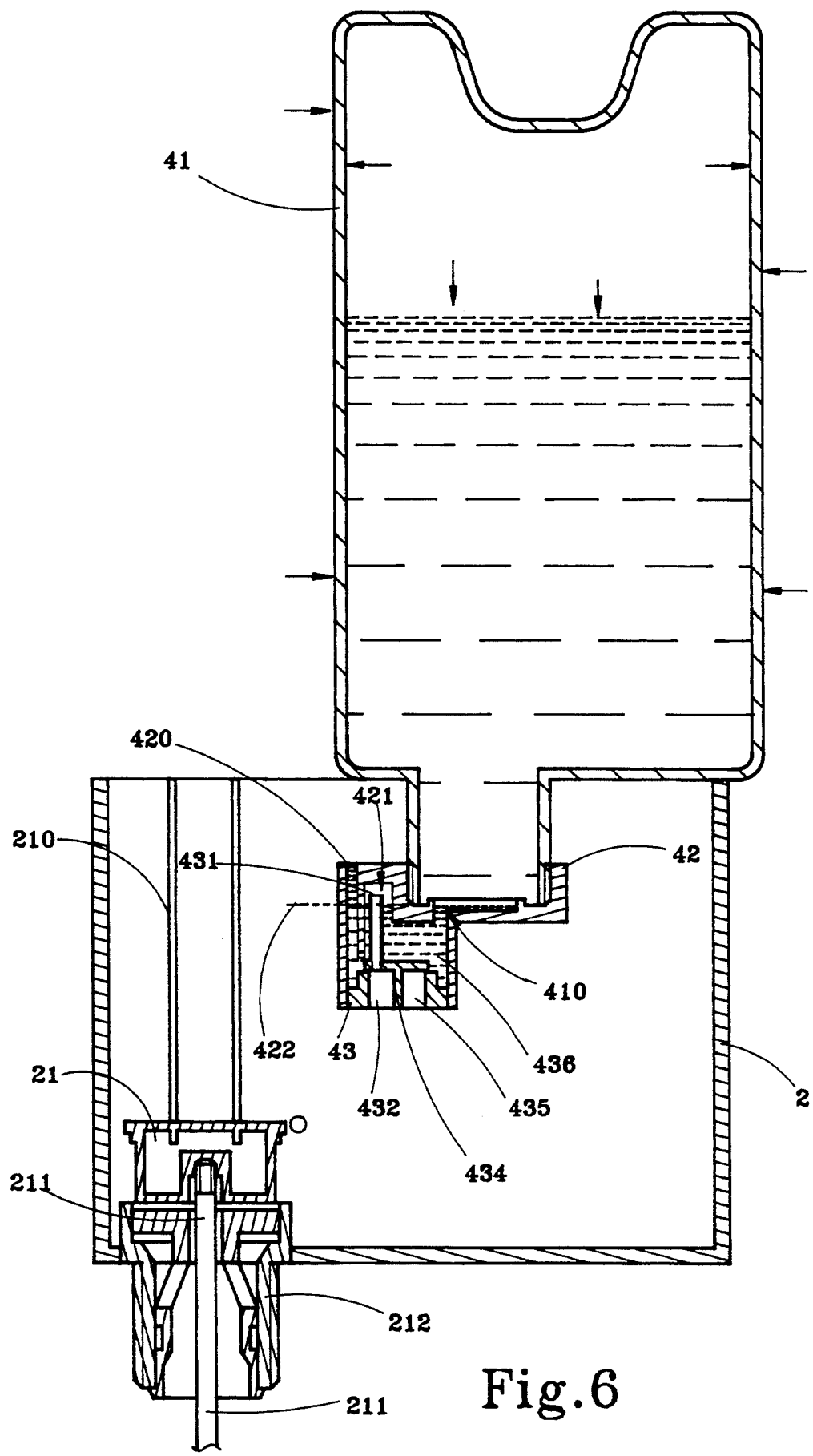
FIG. 6 is a cross sectional view showing the internal structure of the detergent dispensing device and water container of the automatic lavatory detergent and perfume dispenser shown in FIG. 1.

Referring to FIG. 6, when the water container 2 contains no water, only a small amount of the detergent flows out of the transparent detergent container 41 into a preservation chamber 436 inside the dispensing cap 42. The preservation chamber 436 is disposed in communication with the atmosphere by a small through hole 420 on the dispensing cap 42 and a water intake hole 431 on the dispensing valve 43. At this moment, the gravity of the detergent in the transparent detergent container 41 is balanced with the atmosphere pressure, and therefore the detergent is prohibited from flowing out of the detergent container 41 further.

Figure 7:
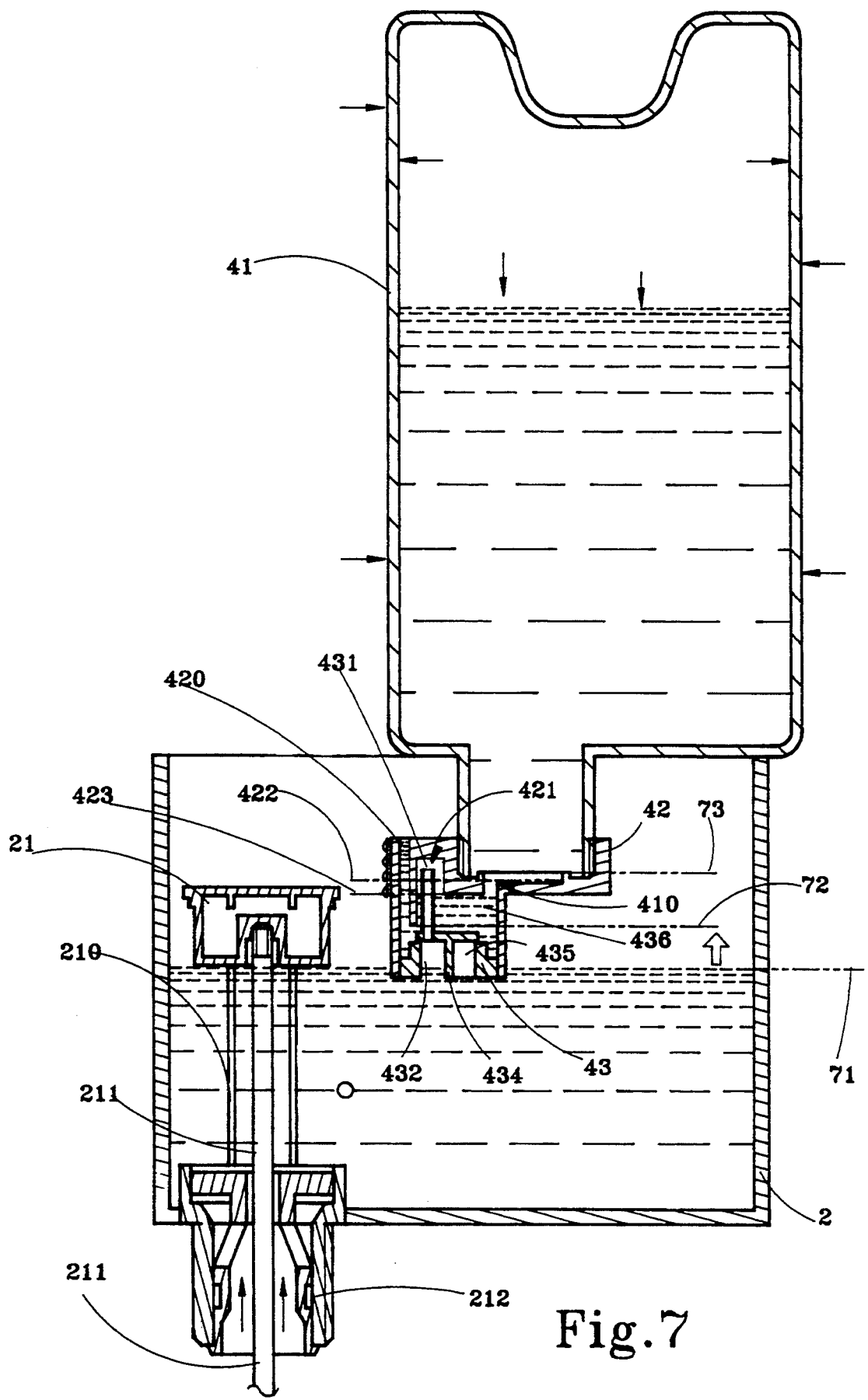
FIG. 7 is similar to FIG. 6 but showing water guided into the water container.

Referring to FIG. 7, when water level rises and touches the bottom of the dispensing valve 43, air in the first air chamber 421 (on the dispensing cap 42) and the second air chamber 432 (in the dispensing valve 43) are forced to compress the preservation chamber 436 causing the detergent in the preservation chamber 436 dropped from elevation 422 to elevation 423, and therefore an equal amount of the detergent is forced to flow out of the dispensing cap 42 through the through hole 420 into the water container 2 for mixing with water. When a fixed amount of the detergent is driven out of the dispensing cap 42, an equal amount of air is forced to flow from the first and second air chambers 421;432 into the detergent container 41. When water level keeps moving to elevation 71, then elevation 72, and then elevation 73, more air is forced into the detergent container. Under this stage, the pressure inside the detergent container is still smaller than the atmosphere pressure, and therefore the detergent does not flow out of the detergent container 41.

Figure 8:
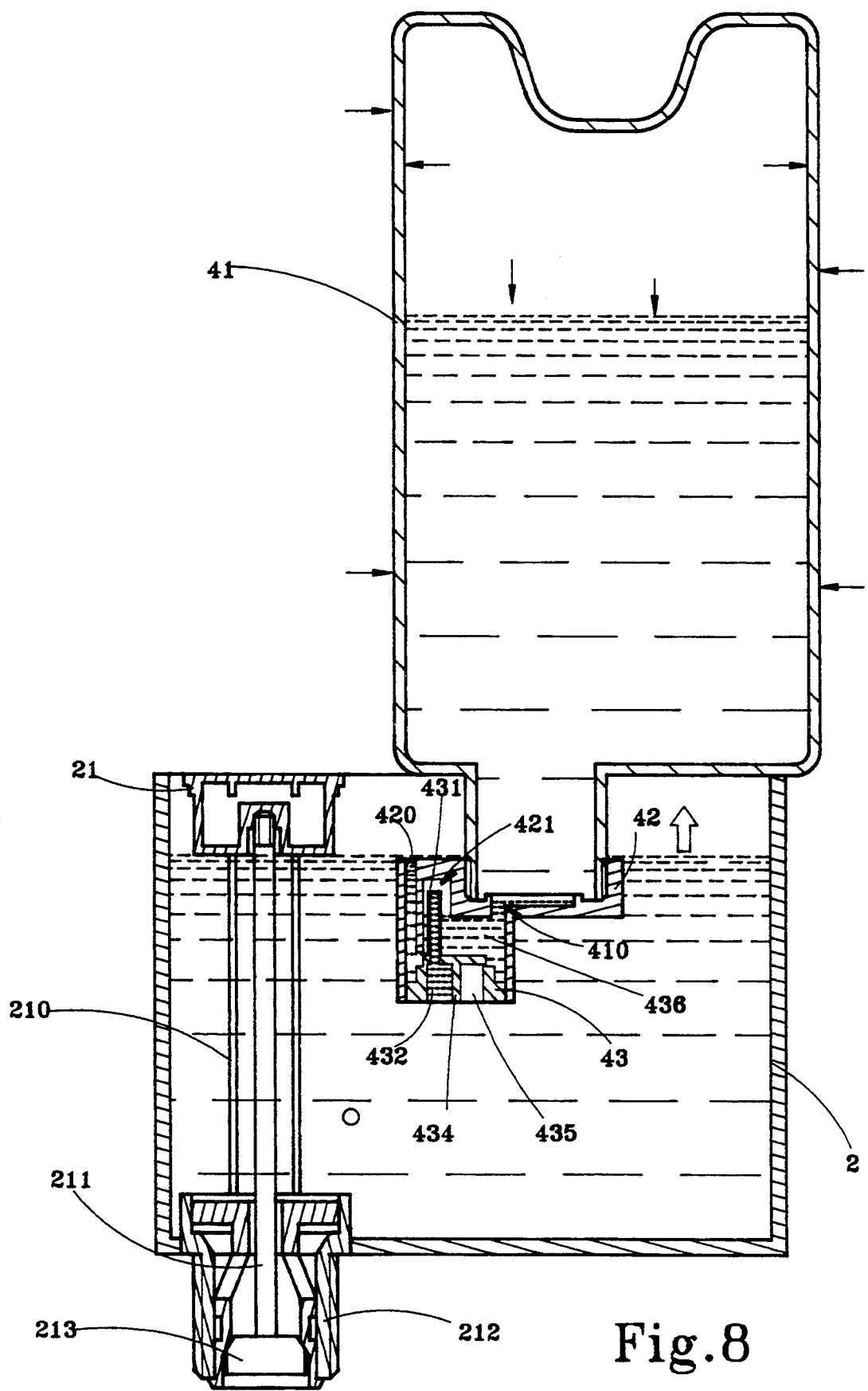
FIG. 8 is similar to FIG. 7 but showing water level moved to the elevation above the dispensing cap.

Referring to FIG. 8, when water level surpasses the water intake hole 431, water flows from the water container 2 into the preservation chamber 436 to mix with the detergent being retained in the preservation chamber 436, and then continuously flows out of the dispensing cap 42 through the through hole 420 into the water container 2 again. Therefore, what contained in the water container 2 in this stage is a detergent solution.

Figure 9:
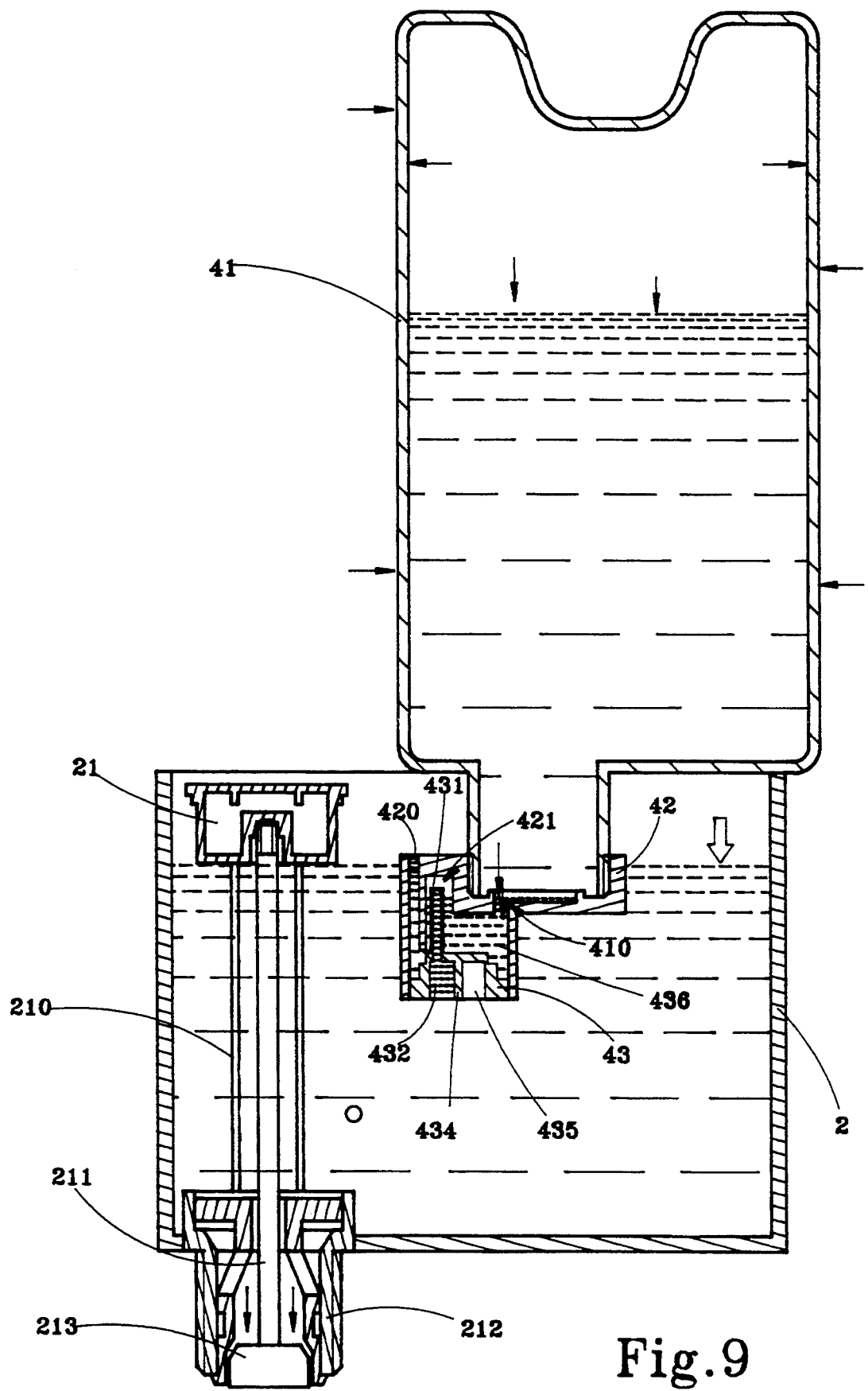
FIG. 9 is similar to FIG. 8 but showing water level being dropped.
Figure 10:
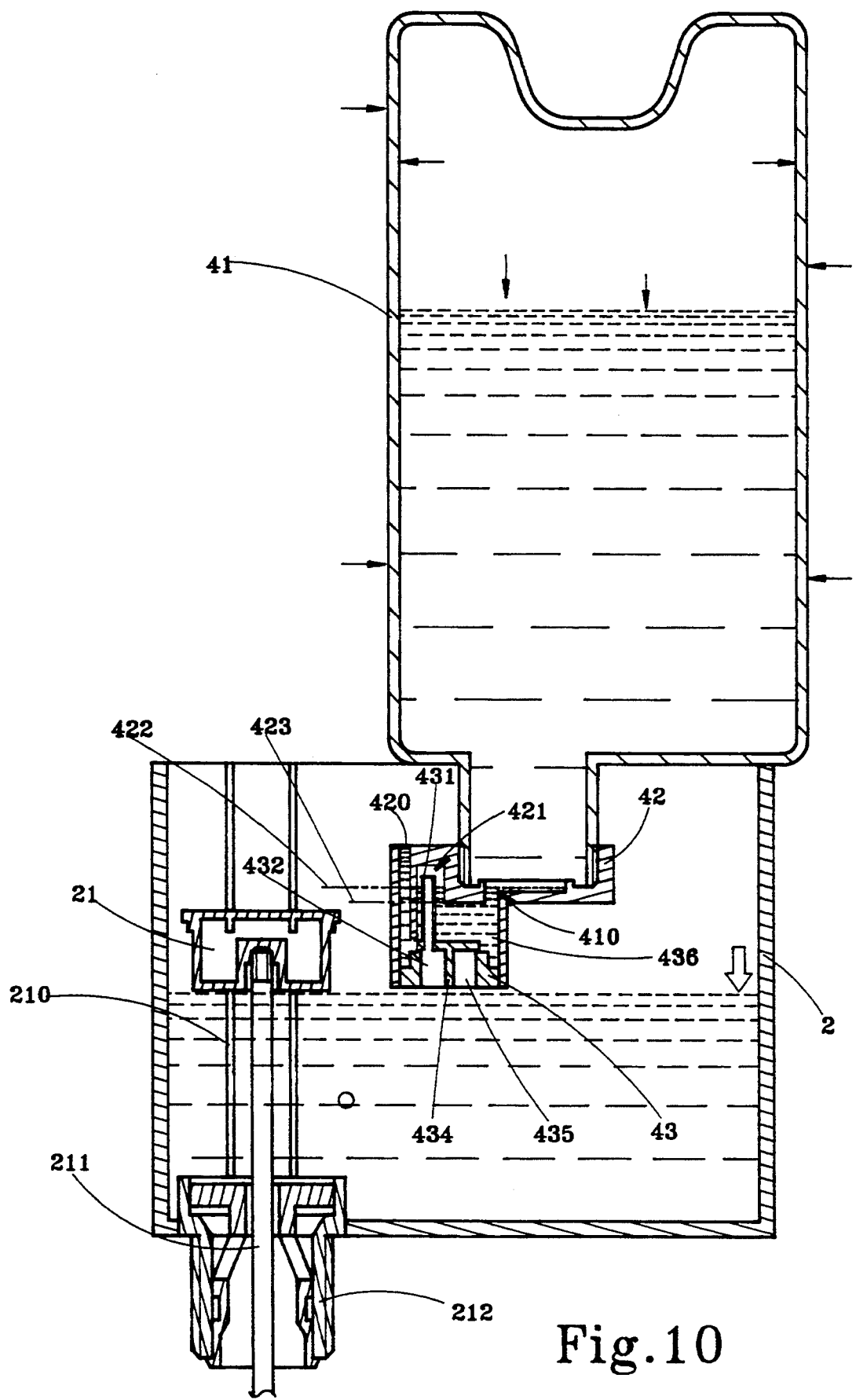
FIG. 10 is similar to FIG. 9 but showing water dropped to the elevation below the bottom of the dispensing cap.

Referring to FIGS. 9 and 10, when water flows back from the water container 2 into the flush pipe 7, the pressure in the detergent container 41 is relatively released, causing a fixed amount of the detergent squeezed out of the detergent container 41 through the bottom opening 410 into the preservation chamber 436. When a fixed amount of the detergent is squeezed out of the detergent container 41 into the preservation chamber 436, the residual detergent solution in the preservation chamber 436 is moved out of the dispensing cap 42 through the through hole 420 into the water container 2. When water level in the water container 2 drops below the elevation of the bottom of the detergent dispensing device 4, air is allowed to enter the first and second air chambers 421;432 again, and therefore the dispensing valve 43 and the dispensing cap 42 are returned to the conditions shown in FIG. 7.

Figure 4:
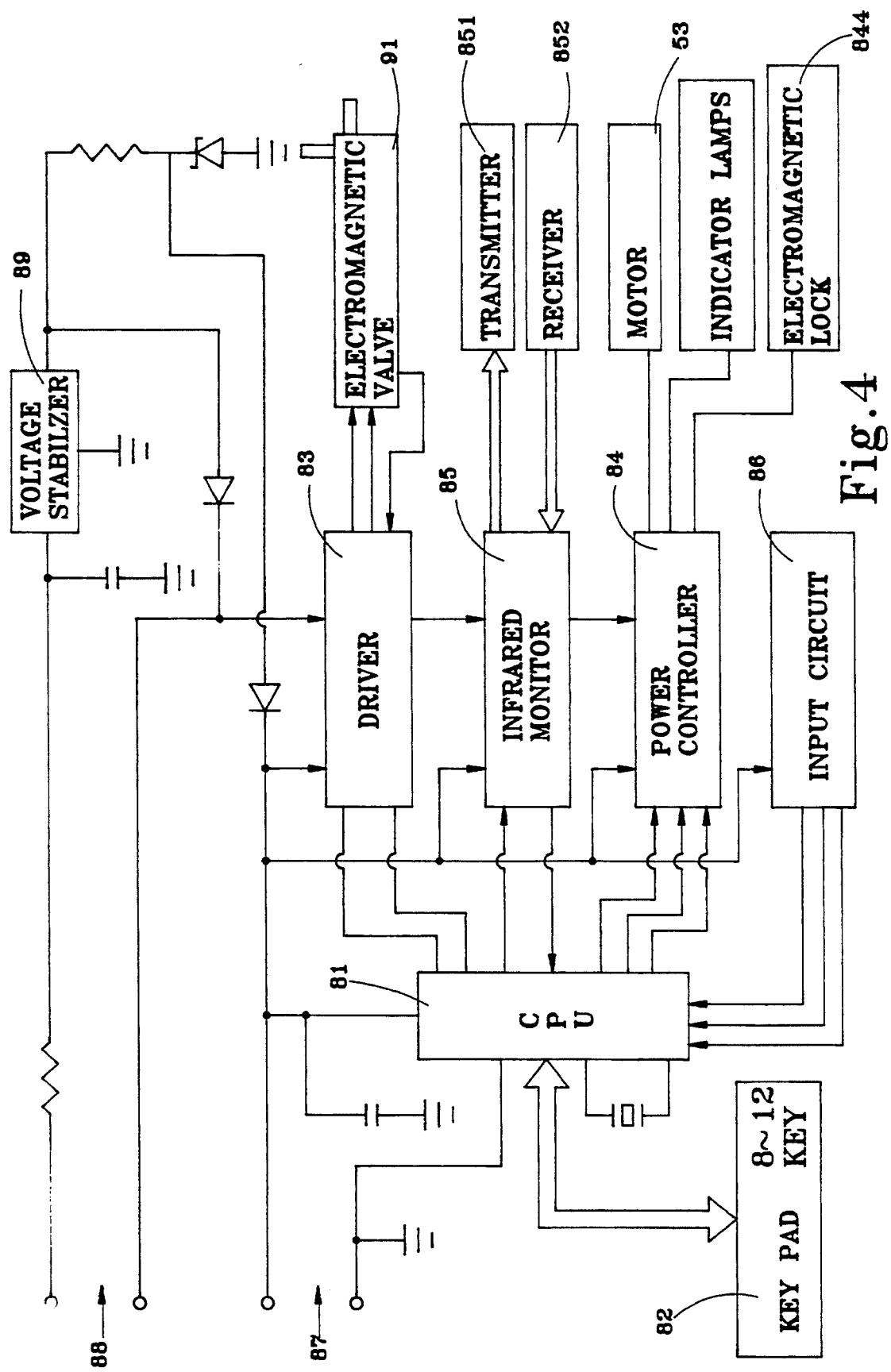
FIG. 4 is a block diagram of the control circuit assembly of the present invention.
Figure 5:
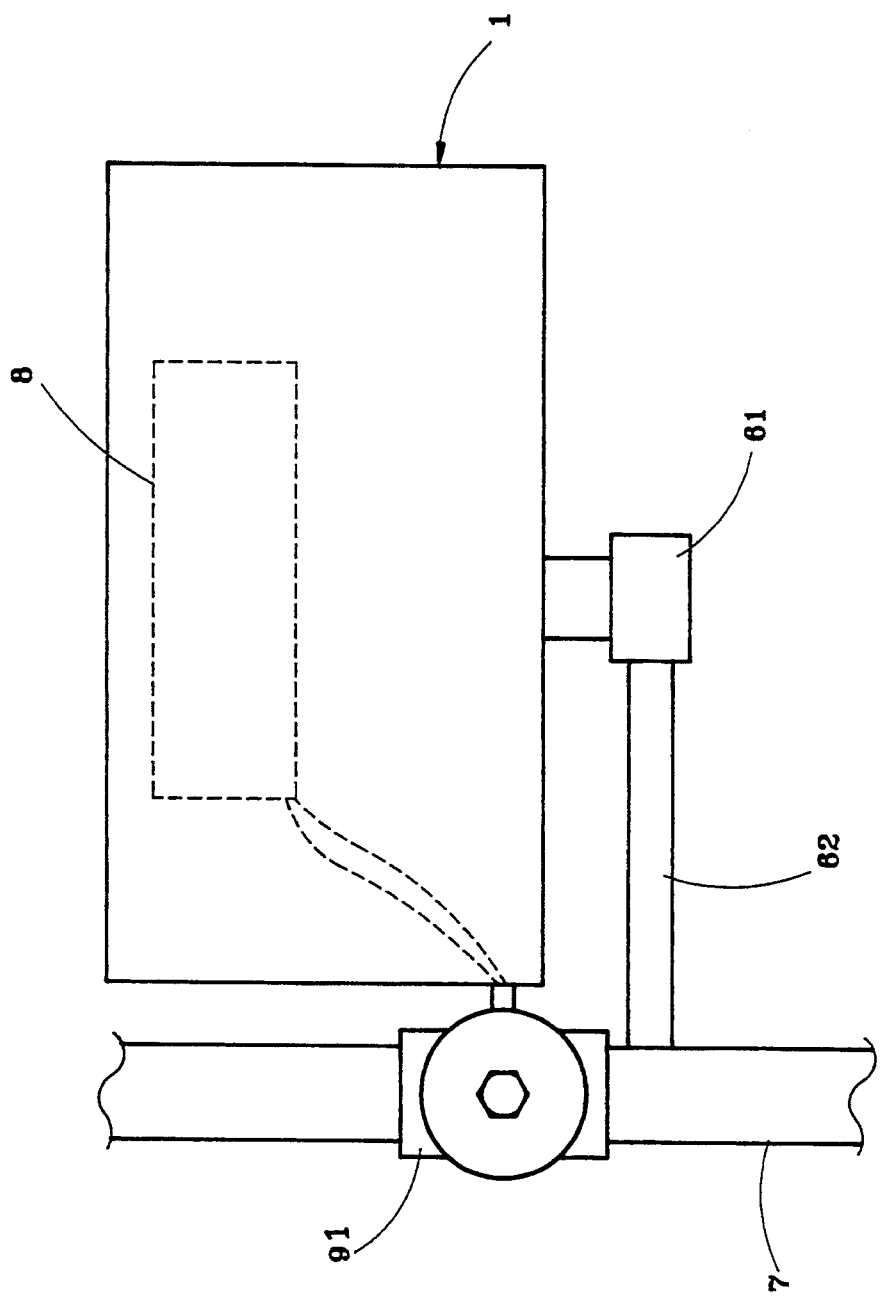
FIG. 5 is a plain view of an electromagnetic valve assembly according to the present invention.

Referring to FIGS. 4 and 5 and FIG. 2 again, the flushing of the flush pipe 7 is controlled by a control circuit assembly 8 via an electromagnetic valve 91. The control circuit assembly 8 uses a non-contact type detector (for example: an infrared monitor) 85 to actuate the electromagnetic valve 91 and the motor 53 being mounted on a motor holder 52 on the vertical wall of the base frame 11 upon the detection of the approach of a human body. When the motor 53 is actuated, a fan 531 is turned on to send a current of air toward a perfume dispensing device 3 causing it to dispense the perfume into the air. The perfume dispensing device 3 comprises a sponge holder 31 having a guide hole 311, a perfume bottle 34 having a bottom hole (not shown) connected to the guide hole 311 by a connector 312, a sponge 32 mounted on the sponge holder 31 to suck in the liquid perfume being guided from the perfume bottle 3 into the guide hole 311 of the sponge holder 31, and a holder cover 33 covered on the sponge holder 31 over the sponge 32.

Referring to FIGS. 1, 3, 4, and 5 again, the control circuit assembly 8 comprises a CPU (central processing unit) 81, a key pad 82, a driver 83, a power controller 84, an infrared monitor 85, and an input circuit 86. The control circuit assembly 8 is mounted inside the housing 1. The key pad 82 comprises three indicator lamps, namely, the flush indicator lamp 821, the flush setting indicator lamp 822, and the sterilization indicator lamp 823 for the indication of the flushing operation and the setting of quaternary ammonium compound. The key pad 82 further comprises a series of touch-control keys 824 for signal input. There is provided an infrared outlet 112 on the housing 1 below the touch-control keys 824 through which the infrared monitor 85 detects the approach of the user. The CPU 81 receives inputted signals from the keys 824 and incorporates with the input circuit 86 to control the operation of the driver 83 and the infrared monitor 85. The input circuit 86 serves as a communication interface for connection to external network, power protection circuit, water level detection circuit, infrared detection circuit, etc. Through the infrared outlet 112, the infrared monitor 85 monitors the operation of an infrared transmitter 851 and an infrared receiver 852. Upon the detection of the approach of a human body, the infrared monitor 85 provides a signal to the CPU 81 causing it to drive the driver 83 in turning on the electromagnetic valve 91 for allowing water to enter from the flush pipe 7 to the water container 2 via the guide pipe 62, to turn on the motor 53 and the three indicator lamps 821;822;823 on the key pad 82, and to unlock an electromagnetic lock 844. The electromagnetic lock 844 locks the housing 1, and is controlled by a programmed signal inputted through the touch-control keys 824. Power supply to the control circuit assembly 8 may be obtained from the battery set (not shown) being mounted on a battery chamber 54 inside the housing 1 via a first power input port 87 or from external power supply through a voltage stabilizer 89 via a second power input port 88. A certain time cycle may be inputted through the touch-control keys 824 of the key pad 82 to intermittently turn on/off the motor 53 and the electromagnetic valve 71.

While only one embodiment of the present invention has been shown and described, it will be understood that various modifications and changes could be made without departing from the spirit and scope of the invention.

I claim:

1. An automatic lavatory detergent and perfume dispenser for connection with a lavatory flush pipe comprising:

a housing having a view window and an exhaust port with a shutter on a front panel thereof;

a water container mounted inside said housing at a bottom thereof, said water container comprising a valve seat at a bottom thereof, a float floated in water in said water container, an upright rod having a top end connected to said float and a bottom end extended out of said valve seat and coupled with a valve cone, said valve cone being moved by said float to control the opening of said valve seat;

a water guide to guide water from the flush pipe into said water container through said valve seat;

a detergent dispensing device disposed inside said housing above said water container, said detergent dispensing device comprising a transparent detergent container having a bottom opening, a dispensing cap fastened to the bottom opening on said detergent container and forced to send a fixed amount of a detergent from said transparent detergent container when water in said water container reaches full water level;

a perfume dispensing device mounted inside said housing behind said shutter, said perfume dispensing device comprising a sponge holder having a guide hole, a perfume bottle having a bottom hole connected to the guide hole on said sponge holder, a sponge mounted on said sponge holder to suck in a liquid perfume being guided from said perfume bottle into the guide hole of said sponge holder, and a DC motor fan driven to send a current of air through said sponge toward said shutter; and a control circuit assembly disposed inside said housing;

wherein said control circuit assembly comprises:

a key pad mounted on said front panel of said housing and comprising a plurality of touch-control keys for setting controls;

an infrared monitor having an infrared transmitter and an infrared receiver respectively mounted on said front panel of said housing to detect the approach of human bodies and to send a detected signal upon the detection of the approach of a human body;

a central processing unit to receive the detected signal from said infrared monitor and to output a control signal upon receipt of the detected signal or at a predetermined cycle being set through said touch-control keys of said key pad;

a driver to receive the control signal from said central processing unit and to output a driving signal upon receipt of the control signal from said central processing unit;

an electromagnetic valve adapted to be installed in said flush pipe and controlled by said driver to let water flow from said flush pipe to said guide tube; and a power controller controlled by the control signal from said central processing unit to turn on said DC motor fan and an indicator lamp for illumination.

2. The control circuit assembly of claim 1 further comprising an electromagnetic lock controlled by said power controller to open said housing, said electromagnetic lock controlled by said touch-control keys to maintain said housing locked.

* * * * *